United States Patent
Nakazawa et al.

(10) Patent No.: US 11,159,913 B2
(45) Date of Patent: Oct. 26, 2021

(54) POSITION ESTIMATION SYSTEM

(71) Applicant: Murata Manufacturing Co., Ltd., Kyoto (JP)

(72) Inventors: Akira Nakazawa, Kyoto (JP); Takashi Ishihara, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 64 days.

(21) Appl. No.: 16/801,273

(22) Filed: Feb. 26, 2020

(65) Prior Publication Data

US 2020/0196109 A1 Jun. 18, 2020

Related U.S. Application Data

(63) Continuation of application No. PCT/JP2018/031020, filed on Aug. 22, 2018.

(30) Foreign Application Priority Data

Aug. 31, 2017 (JP) .............................. JP2017-167165

(51) Int. Cl.
*H04W 4/029* (2018.01)
*G01S 5/14* (2006.01)

(52) U.S. Cl.
CPC .............. *H04W 4/029* (2018.02); *G01S 5/14* (2013.01)

(58) Field of Classification Search
CPC ........... H04W 4/029; H04W 4/80; G01S 5/14; G01S 5/02; G01S 5/0295; G01S 5/0226; G01S 2205/02; G06Q 50/04; G06Q 50/22; Y02P 90/30; G16H 40/20

USPC ...................................................... 455/456.1
See application file for complete search history.

(56) References Cited

U.S. PATENT DOCUMENTS

| | | | |
|---|---|---|---|
| 2002/0198986 A1 | 12/2002 | Dempsey | |
| 2005/0176406 A1* | 8/2005 | Krishnakumar | G01S 5/02 455/410 |
| 2011/0210167 A1 | 9/2011 | Lyon | |
| 2013/0225200 A1 | 8/2013 | Hamida et al. | |
| 2015/0145728 A1* | 5/2015 | Addison | G01S 5/14 342/465 |

(Continued)

FOREIGN PATENT DOCUMENTS

| | | | |
|---|---|---|---|
| JP | 2005-512017 A | 4/2005 | |
| JP | 2014-502339 A | 1/2014 | |

(Continued)

OTHER PUBLICATIONS

International Search Report for International Application No. PCT/JP2018/031020 dated Nov. 20, 2018.

(Continued)

*Primary Examiner* — Farid Seyedvosoghi
(74) *Attorney, Agent, or Firm* — Pearne & Gordon LLP

(57) ABSTRACT

The position of a transmission device is estimated with a sufficient accuracy. A position estimation system includes a transmission device that includes a plurality of transmitters arranged symmetrically with respect to a specific reference position, a plurality of receivers that receive radio waves transmitted from the plurality of transmitters, and an estimation tool that estimates the position of the transmission device, based on reception strengths of the radio waves received at the receivers.

7 Claims, 5 Drawing Sheets

(56) References Cited

U.S. PATENT DOCUMENTS

| | | | | |
|---|---|---|---|---|
| 2015/0172872 A1* | 6/2015 | Alsehly | ................. | H04W 4/33 |
| | | | | 455/457 |
| 2016/0260059 A1* | 9/2016 | Benjamin | ............ | H04W 4/027 |
| 2017/0026794 A1 | 1/2017 | Baker et al. | | |
| 2018/0316445 A1 | 11/2018 | Hamada et al. | | |

FOREIGN PATENT DOCUMENTS

| | | |
|---|---|---|
| JP | 2015-224943 A | 12/2015 |
| JP | 2017-015577 A | 1/2017 |
| JP | 2017-116389 A | 6/2017 |
| JP | 6142099 B1 | 6/2017 |
| WO | 2017/069138 A1 | 4/2017 |

OTHER PUBLICATIONS

Written Opinion for International Application No. PCT/JP2018/031020 dated Nov. 20, 2018.
Notice of Reasons for Rejection for JP Patent Application No. 2019-539414 dated Mar. 19, 2021.

\* cited by examiner

| FACILITY NAME | OPERATING STATE | MTBF | OPERATOR |
|---|---|---|---|
| A | RUNNING | ○○ MINUTES | X |
| B | RUNNING | ×× MINUTES | |
| C | STOPPED | △△ MINUTES | Y |
| ⋮ | ⋮ | ⋮ | ⋮ |
| G | RUNNING | ○× MINUTES | Z |
| H | RUNNING | △○ MINUTES | |

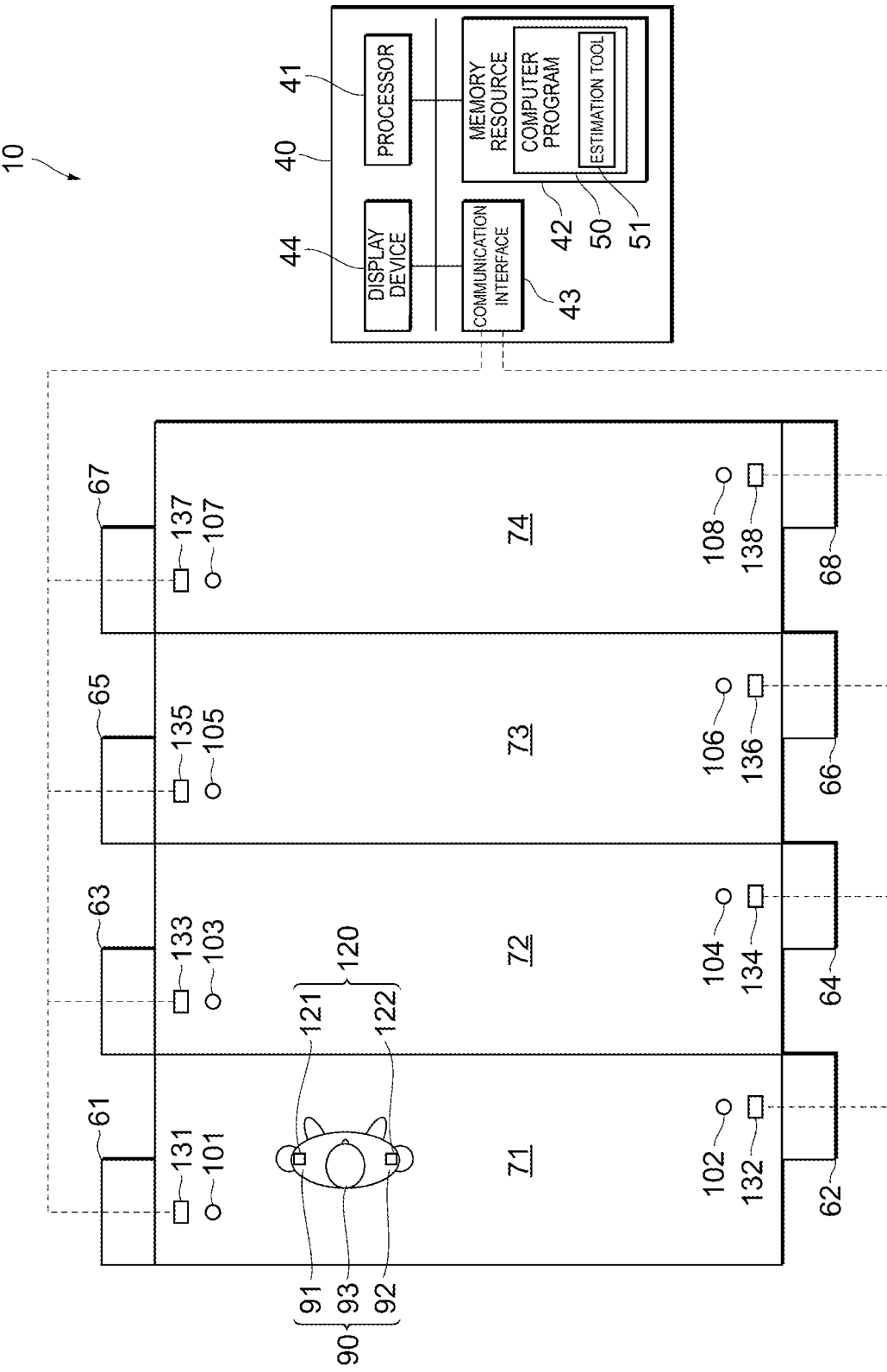

POSITION ESTIMATION SYSTEM

This is a continuation of International Application No. PCT/JP2018/031020 filed on Aug. 22, 2018 which claims priority from Japanese Patent Application No. 2017-167165 filed on Aug. 31, 2017. The contents of these applications are incorporated herein by reference in their entireties.

BACKGROUND

Technical Field

The present disclosure relates to a position estimation system.

A technique for estimating a position of a transmitter through radio communication between the transmitter and a receiver has been known. For example, a position estimation system described in Patent Document 1 includes a plurality of transmitters that transmit beacon signals carrying identification information at substantially the same transmission power and a receiver that is able to move along a direction in which the plurality of transmitters are arranged. The receiver stores, as a first threshold, the average value of reception strengths at which the beacon signals are received near the transmitters and stores, as a second threshold, the average value of reception strengths at which the beacon signals are received in between adjacent transmitters. The receiver compares a reception strength of a beacon signal received from a transmitter with each of the first threshold and the second threshold, and thus estimates the current position of the receiver. Meanwhile, a position estimation system described in Patent Document 2 collects, at an access point, reception strengths at which one of a plurality of communication terminals including mobile communication terminals performs reception from another one of the plurality of communication terminals, and performs statistical processing. Accordingly, a deterioration in the accuracy in estimation of the position of a mobile communication terminal can be reduced.

Patent Document 1: Japanese Unexamined Patent Application Publication No. 2015-224943

Patent Document 2: Japanese Unexamined Patent Application Publication No. 2017-15577

BRIEF SUMMARY

However, the position estimation system described in Patent Document 1 sets the first threshold and the second threshold based on actual measurement values of the reception strengths of beacon signals, and therefore, needs to measure the reception strengths of the beacon signals every time that the reception environment of radio waves change. Furthermore, under an environment in which there are many objects that shield or reflect radio waves, such as inside a plant or an office, it is difficult to estimate the accurate position of the receiver, due to influence of multipath phasing. Meanwhile, the position estimation system described in Patent Document 2 requires time for the statistical processing, and therefore, is not suitable for real-time estimation of position.

Furthermore, in a position estimation system of this type, if directivities of radio waves from transmitters are not uniform, strengths of radio waves received at a receiver differ significantly from one another even according to the orientations of the transmitters even at the same position, and the accuracy in estimation of the position of a transmitter may thus decrease.

The present disclosure estimates the position of a transmission device with a sufficient accuracy.

A position estimation system according to the present disclosure includes a transmission device that includes a plurality of transmitters arranged symmetrically with respect to a specific reference position; a plurality of receivers that receive radio waves transmitted from the plurality of transmitters; and an estimation unit that estimates a position of the transmission device, based on reception strengths of the radio waves received at the receivers.

With a position estimation system according to the present disclosure, the position of a transmission device can be estimated with a sufficient accuracy.

BRIEF DESCRIPTION OF THE SEVERAL VIEWS OF THE DRAWINGS

FIG. 7 is an explanatory diagram illustrating another example of a configuration of a position estimation system according to an embodiment of the present disclosure.

DETAILED DESCRIPTION

Hereinafter, embodiments of the present disclosure will be described with reference to drawings. Same signs represent same component elements, and redundant explanation will be omitted.

Figure 1:
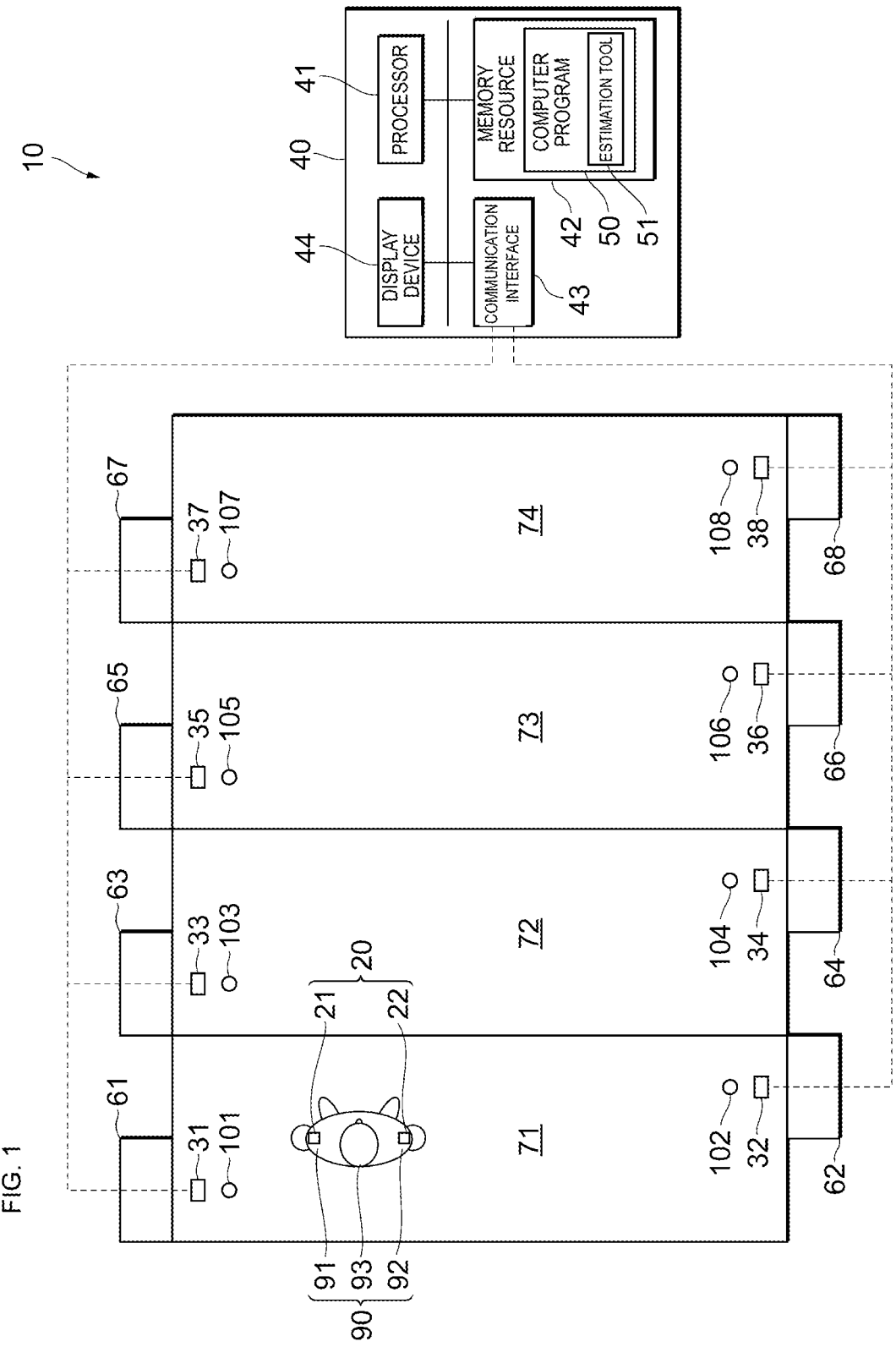
FIG. 1 is an explanatory diagram illustrating an example of a position estimation system according to an embodiment of the present disclosure.

FIG. 1 is an explanatory diagram illustrating a configuration of a position estimation system 10 according to an embodiment of the present disclosure. The position estimation system 10 includes a transmission device 20, a plurality of receivers 31 to 38, and a computer system 40. The transmission device 20 is movable and the location of the transmission device 20 is unknown. In contrast, the plurality of receivers 31 to 38 are fixed at specific positions, and the locations of the plurality of receivers 31 to 38 are known. The transmission device 20 broadcasts a beacon signal carrying identification information unique to the transmission device 20 in all directions. The plurality of receivers 31 to 38, each receives the beacon signal from the transmission device 20 and outputs an RSSI (Received Signal Strength Indication), which is information regarding the reception strength of the beacon signal, to the computer system 40. The computer system 40 estimates the current position of the transmission device 20, based on the RSSI output from each of the receivers 31 to 38. Short-range radio communication standards (for example, Wifi (Wireless Fidelity) (registered trademark), UWB (Ultra Wide Band), Bluetooth (registered trademark), Bluetooth Low Energy, or the like) may be used as communication standards used between the transmission device 20 and the receivers 31 to 38.

The computer system 40 includes a processor 41, a memory resource 42, a communication interface 43, and a display device 44. The memory resource 42 is a memory region for a computer-readable recording medium (for example, a hard disk drive, a solid state drive, a memory card, an optical disc drive, a semiconductor memory, or the like). A computer program 50 for controlling an operation of the computer system 40 is stored in the memory resource 42. The computer program 50 includes an estimation tool 51, which is a software module that receives, through the communication interface 43, an RSSI output from each of the receivers 31 to 38 and estimates the position of the transmission device 20, based on the RSSI. The processor 41 functions as an estimation unit that estimates the position of the transmission device 20 by analyzing and executing the estimation tool 51. As described above, a function as the estimation unit that estimates the position of the transmission device 20 is implemented by cooperation between the processor 41 and the estimation tool 51. However, a similar function may be implemented by using a dedicated hardware resource (for example, an application specific integrated circuit (ASIC)) or firmware.

Figures 2, 3:
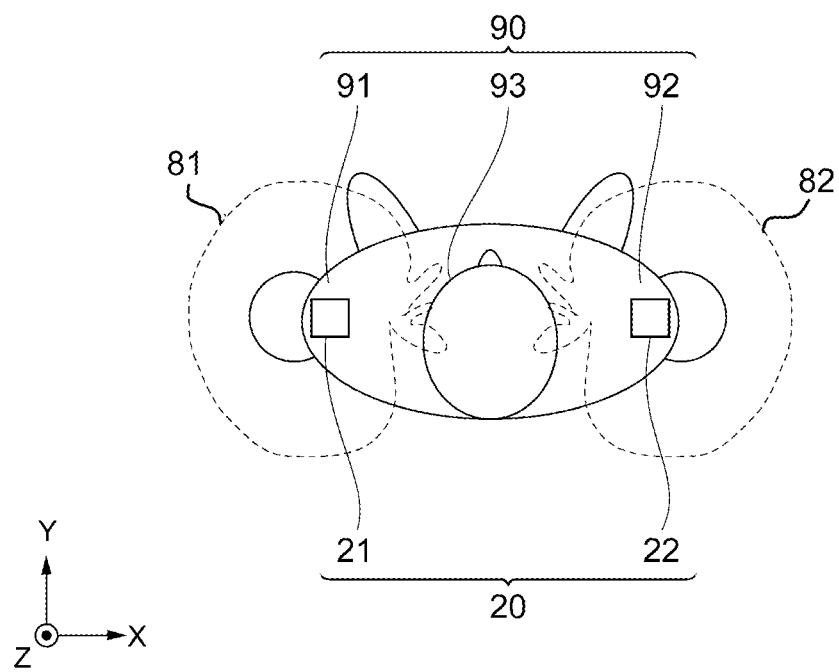
FIG. 2 is an explanatory diagram illustrating a configuration of a transmission device in a position estimation system according to an embodiment of the present disclosure.
FIG. 3 is an explanatory diagram of a screen displayed on a display device of a position estimation system according to an embodiment of the present disclosure.

Now, details of the transmission device 20 will be described with reference to FIG. 2. In FIG. 2, an example in which the transmission device 20 is attached to a human body 90 is illustrated. In FIG. 2, an X-Y plane is parallel to a horizontal plane, a Z direction is parallel to a vertical direction, and the human body 90 stands up parallel to the vertical direction. The transmission device 20 includes a plurality of transmitters 21 and 22 that broadcast the same beacon signals carrying identification information unique to the transmission device 20 in all directions. The plurality of transmitters 21 and 22, each includes an antenna (for example, a monopole antenna, a plate-shaped inverted F antenna, or the like) that broadcasts a beacon signal in all directions. In the example illustrated in FIG. 2, the transmitters 21 and 22 are attached to shoulders 91 and 92 with a head part 93 therebetween. Signs 81 and 82 denote directivities of radio waves from the transmitters 21 and 22, respectively. As illustrated in FIG. 2, part of the radio waves is shielded or attenuated by the head part 93. Therefore, if only one of the transmitters 21 and 22 is attached to the human body 90, the directivities 81 and 82 of the radio waves are not uniform. In the case where the directivities 81 and 82 of the radio waves from the transmitters 21 and 22 are not uniform, even when the position of the human body 90 is the same, the reception strengths of beacon signals received at the receivers 31 to 38 differ significantly from one another according to the orientations of the transmitters 21 and 22, and the accuracy in estimation of the position of the transmission device 20 may be reduced. Thus, the plurality of transmitters 21 and 22 are arranged symmetrically with respect to a specific reference position (for example, the head part 93). Accordingly, the non-uniformity of the directivities 81 and 82 of the transmission radio waves can be compensated for. For example, in the example illustrated in FIG. 2, a shortage of transmission power from the transmitter 21 to a +X direction can be compensated for by the transmitter 22. In a similar manner, a shortage of transmission power from the transmitter 22 to a −X direction can be compensated for by the transmitter 21. With such an arrangement, the plurality of transmitters 21 and 22 are able to emit radio waves uniformly, as a whole, in all directions parallel to the X-Y plane. Therefore, the radio waves are substantially non-directional. Accordingly, variations in the RSSIs of the receivers 31 to 38 according to a difference in the orientations of the transmitters 21 and 22 can be reduced, and the accuracy in estimation of the position of the transmission device 20 can be increased.

The way that the transmitters 21 and 22 are arranged symmetrically with respect to the reference position is not limited to the example illustrated in FIG. 2. For example, the transmitters 21 and 22 may be arranged in both upper arm parts of the human body 90, may be arranged in a chest part and a back part of the human body 90, or may be arranged in a front part of the head and a back part of the head of the human body 90. Furthermore, the reference position for the case where the transmitters 21 and 22 are attached to the human body 90 is not necessarily the head part 93. Any part of the human body 90 may be defined as the reference position. Furthermore, the reference position for the case where the transmitters 21 and 22 are mounted on a mobile body (for example, a truck) may be any part of the mobile body.

FIG. 1 will be explained below again. The human body 90 represents an operator who manipulates the operation of plant facilities 61 to 68 while moving in a plant. The plant facilities 61 to 68 are, for example, programmable logic controllers that execute software written in a programming language configured by symbolizing a relay circuit called a ladder diagram. Signs 71 to 74 denote areas (physical regions) including positions 101 to 108 through which the human body 90 as the operator is expected to pass. The plurality of receivers 31 to 38 are formed into groups associated with the corresponding areas. For example, the receivers 31 and 32 are arranged in the area 71 and are formed into a group associated with the area 71. The area 71 includes the positions 101 and 102, the receiver 31 is arranged near the plant facility 61 adjacent to the position 101, and the receiver 32 is arranged near the plant facility 62 adjacent to the position 102. The receivers 33 and 34 are arranged in the area 72 and are formed into a group associated with the area 72. The area 72 includes the positions 103 and 104, the receiver 33 is arranged near the plant facility 63 adjacent to the position 103, and the receiver 34 is arranged near the plant facility 64 adjacent to the position 104. The receivers 35 and 36 are arranged in the area 73 and are formed into a group associated with the area 73. The area 73 includes the positions 105 and 106, the receiver 35 is arranged near the plant facility 65 adjacent to the position 105, and the receiver 36 is arranged near the plant facility 66 adjacent to the position 106. The receivers 37 and 38 are arranged in the area 74 and are formed into a group associated with the area 74. The area 74 includes the positions 107 and 108, the receiver 37 is arranged near the plant facility 67 adjacent to the position 107, and the receiver 38 is arranged near the plant facility 68 adjacent to the position 108.

The estimation tool 51 estimates an area in which the transmission device 20 is located, based on the average value of RSSIs for each group. The estimation tool 51 determines the highest average value from among, for example, the average value of RSSIs output from the receivers 31 and 32, the average value of RSSIs output from the receivers 33 and 34, the average value of RSSIs output from the receivers 35 and 36, and the average value of RSSIs output from the receivers 37 and 38. Then, the estimation tool 51 estimates that the transmission device 20 is located in the area associated with the group of the receivers with the highest average value of the output RSSIs. Next, the estimation tool 51 performs comparison between the RSSIs output from the plurality of receivers in the group associated with the area in which the transmission device 20 is estimated to be located and thus estimates an approximate position in the area in which the transmission device 20 is located. For example, in the case where the average value of the RSSIs output from the receivers 31 and 32 is the highest, the estimation tool 51 estimates that the transmission device 20 is located in the area 71. Then, in the case where the RSSI output from the receiver 31 is higher than the RSSI output from the receiver 32, the estimation tool 51 estimates that the transmission device 20 is located near the position 101.

The display device 44 displays the position of the human body 90 as the operator and operating statuses of the plant facilities 61 to 68 in such a manner that the position of the human body 90 is associated with the operating status of each of the plant facilities 61 to 68. A plurality of operators may perform an operation in the areas 71 to 74. Each operator can be identified based on identification information superimposed on a beacon signal transmitted from the transmission device 20 attached to the operator. FIG. 3 illustrates an example of a screen displayed on the display device 44. In FIG. 3, names "A" to "H" of the plant facilities 61 to 68 are indicated in a "Facility Name" field. Information indicating whether a plant facility is running or stopped is indicated in an "Operating Status" field. An average mean time between failures of a plant facility is indicated in an "MTBF" field. An identification symbol of an operator located near a position adjacent to a plant facility is indicated in an "Operator" field. For example, the screen illustrated in FIG. 3 indicates that the operator identified with an identification symbol "X" is located near the position 101 adjacent to the plant facility 61 with a facility name "A". Accordingly, an operation history indicating which operator performed an operation at which time and in which plant facility can be obtained, and the operation history can be useful for improving operation efficiency.

In the case where, due to influence of a shield against radio waves or the like, the reception strength of radio waves received at each of the receivers 31 to 38 is not sufficient to estimate the position of an operator, the estimation tool 51 may estimate the position of the operator, based on the operating status of the plant facilities 61 to 68. For example, in the case where a shield against radio waves is placed near the plant facility 61 and, due to the influence of the shield, the reception strength of radio waves received at the receiver 31 is not sufficient to estimate the position of an operator, if the plant facility 61 is running, the estimation tool 51 may estimate that the operator is located near the position 101 adjacent to the plant facility 61.

In the position estimation system 10 according to this embodiment, the plurality of transmitters 21 and 22 are arranged such that the non-uniformity of the directivities 81 and 82 of radio waves is compensated for. Therefore, variations in the RSSIs of the receivers 31 to 38 according to a difference in the orientation of the transmitters 21 and 22 can be reduced, and the accuracy in estimation of the position of the transmission device 20 can thus be increased. Furthermore, to estimate the position of the transmission device 20, radio waves from only one of the plurality of transmitters 21 and 22 needs to be received. Therefore, there is an advantage of being less susceptible to the influence of a shield against radio waves. Furthermore, to estimate the position of the transmission device 20, a complicated calculation such as statistical processing is not necessary. Therefore, the position of the transmission device 20 can be estimated in real-time and quickly. Moreover, the plurality of receivers 31 to 38 are formed into groups associated with corresponding areas and are not affected by receivers associated with different areas. Therefore, influence of multipath phasing can be reduced.

Next, measurement results of estimation of the position of the transmission device 20 obtained by the position estimation system 10 will be explained with reference to FIGS. 4 to 6.

Figure 4:
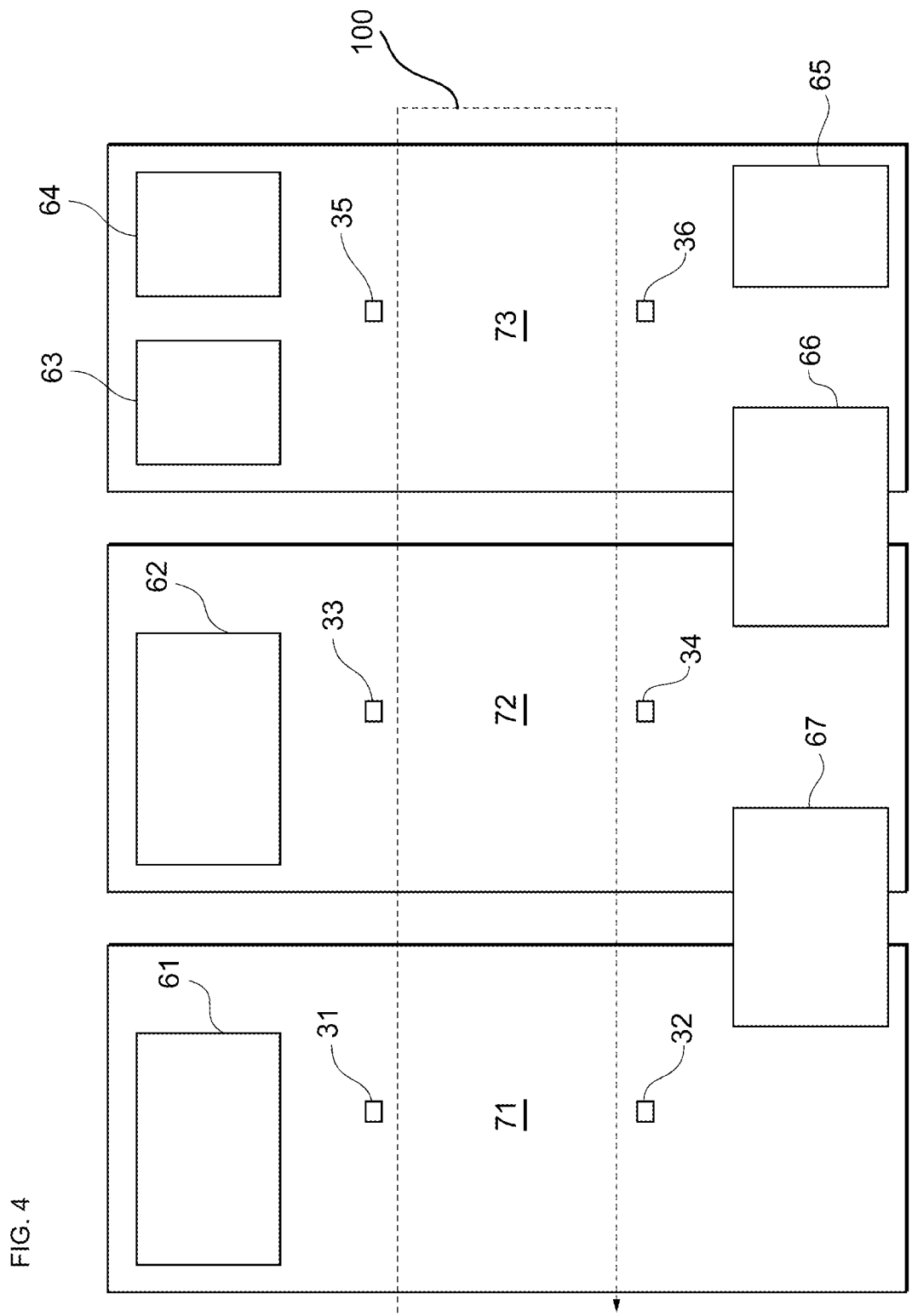
FIG. 4 is an explanatory diagram illustrating an example of an arrangement of receivers according to an embodiment of the present disclosure.

A layout illustrated in FIG. 4 is different from the layout illustrated in FIG. 1 in that the area 74 is omitted and the way that the facilities 61 to 67 are arranged is different from that in FIG. 1. However, the configuration illustrated in FIG. 4 is the same as the configuration illustrated in FIG. 1 except the features mentioned above. For example, although the computer system 40 is not illustrated in FIG. 4, the receivers 31 to 36 are connected to the computer system 40. In FIG. 4, a sign 100 denotes a movement path of the human body 90 on which the transmission device 20 is mounted.

Figure 5:
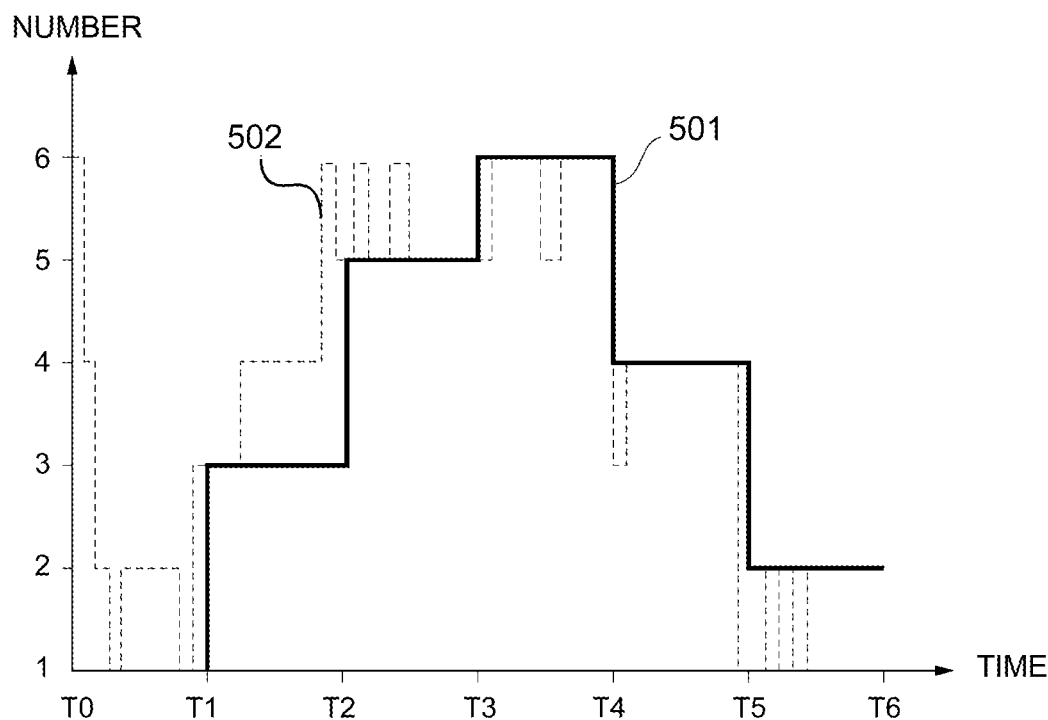
FIG. 5 is a graph illustrating a measurement result for each receiver according to an embodiment of the present disclosure.

FIG. 5 is a graph indicating a measurement result for each receiver. The receivers 31 to 36 are allocated numbers "1" to "6", and the vertical axis of the graph in FIG. 5 represents the number of the receiver closest to the position of the transmission device 20 estimated based on RSSIs. Furthermore, the horizontal axis of the graph in FIG. 5 represents time. A graph represented by a sign 501 indicates an ideal measurement result for each receiver. In the example illustrated in FIG. 4, the terminal apparatus 20 passes by the receivers 31, 33, 35, 36, 34, and 32 in this order along the movement path 100. In the graph 501, the transmission device 20 passes by the receiver 31 during a period from time T0 to time T1. The transmission device 20 passes by the receiver 33 during a period from the time T1 to time T2. The transmission device 20 passes by the receiver 35 during a period from the time T2 to time T3. The transmission device 20 passes by the receiver 36 during a period from the time T3 to time T4. The transmission device 20 passes by the receiver 34 during a period from the time T4 to time T5. The transmission device 20 passes by the receiver 32 during a period from the time T5 to time T6. In contrast, a graph represented by a sign 502 indicates an actual measurement result for each receiver.

Figure 6:
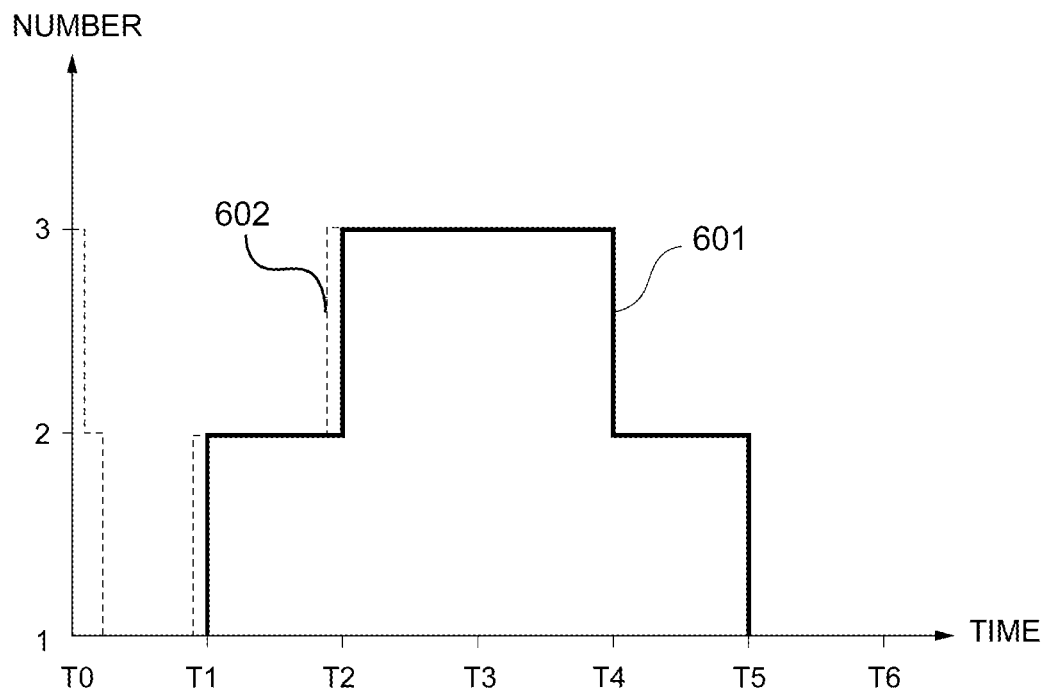
FIG. 6 is a graph illustrating a measurement result for each area according to an embodiment of the present disclosure.

FIG. 6 is a graph indicating a measurement result for each area. The areas 71 to 73 are allocated numbers "1" to "3", and the vertical axis of the graph in FIG. 6 represents the number of the area closest to the position of the transmission device 20 estimated based on RSSIs. Furthermore, the horizontal axis of the graph in FIG. 6 represents time. A graph represented by a sign 601 indicates an ideal measurement result. In the example illustrated in FIG. 6, the transmission device 20 passes through the areas 71, 72, 73, 72, and 71 in this order along the movement path 100. In the graph 601, the transmitter 20 passes through the area 71 during a period from time T0 to time T1. The transmission device 20 passes through the area 72 during a period from the time T1 to time T2. The transmission device 20 passes through the area 73 during a period from the time T2 to time T4. The transmission device 20 passes through the area 72 during a period from the time T4 to time T5. The transmission device 20 passes through the area 71 during a period from the time T5 to time T6. In contrast, a graph represented by a sign 602 indicates an actual measurement result for each area.

When comparing the result in FIG. 5 with the result in FIG. 6, a difference between the actual measurement result 602 for each area and the ideal measurement result 601 for each area is smaller than a difference between the actual measurement result 502 for each receiver and the ideal measurement result 501 for each receiver. Therefore, it is clear that forming the receivers 31 to 36 into groups is useful for improving the accuracy in estimation of the position of the transmission device 20. By estimating the position of an operator based on the operating statuses of the plant facilities 61 to 67 as well as forming the receivers 31 to 36 into groups, the accuracy in estimation of the position of the operator can further be increased.

Furthermore, by arranging receivers such that the transmission device 20 passes through between at least two receivers in the same area (for example, between the receivers 31 and 32 in the area 71) and comparing measurement signals (RSSIs) of the two receivers, a side of the area on which the transmission device 20 is located can be estimated.

In the explanation provided above, the example in which the transmission device 20 moves and the positions of the receivers 31 to 38 are fixed is described. However, the present disclosure is also applicable to an example in which a reception device moves and positions of transmitters are fixed. FIG. 7 illustrates such an example. A sign 120 denotes a movable reception device and the location of the reception device is unknown. In contrast, signs 131 to 138 denote transmitters whose positions are fixed, and locations of the transmitters 131 to 138 are known. Each of the transmitters 131 to 138 transmits, for example, a beacon signal carrying unique identification information in all directions. When receiving a beacon signal from each of the transmitters 131 to 138, the reception device 120 outputs an RSSI, which is information regarding reception strength of the beacon signal, along with identification information included in the received beacon signal and information regarding the time at which the beacon signal was received, to the computer system 40. The computer system 40 estimates the current position of the reception device 120, based on the various types information output from the reception device 120 (for example, the information indicating the RSSI of the beacon signal received by the reception device 120, the identification information included in the beacon signal received by the reception device 120, and the information regarding the reception time of the beacon signal received by the reception device 120). A method for estimating the position of the reception device 120 is similar to the method for estimating the position of the transmission device 20.

The reception device 120 includes a plurality of receivers 121 and 122 that receive beacon signals from the transmitters 131 to 138. The reception device 120 is, for example, able to be attached to the human body 90 as an operator. In this case, the plurality of receivers 121 and 122 are arranged symmetrically with respect to a specific reference position (for example, the head part 93). For example, the receivers 121 and 122 may be arranged in both upper arm parts of the human body 90, may be arranged in a chest part and a back part of the human body 90, or may be arranged in a front part of the head and a back part of the head of the human body 90. Furthermore, the reference position for the case where the receivers 121 and 122 are attached to the human body 90 is not necessarily the head part 93. Any part of the human body 90 may be defined as the reference position. Furthermore, the reference position for the case where the receivers 121 and 122 are mounted on a mobile body (for example, a truck) may be any part of the mobile body. Accordingly, non-uniformity of directivities of reception radio waves can be compensated for, and substantially a non-directional reception sensitivity can be achieved.

In the explanation provided above, the example in which the transmission device 20 is attached to an operator who moves in a plant is described. However, the transmission device 20 may be attached to a component delivery truck that moves in a plant. Accordingly, in the light of the waiting time for the operator or the component delivery truck, the operating status of a plant facility, and the like, this configuration can be useful for improving the operation efficiency. Furthermore, the transmission device 20 may be attached to a health care provider, a patient, or medical equipment that moves in a hospital. Accordingly, the location of the health care provider, the patient, or the medical equipment that moves in the hospital can be acquired, and this configuration can be useful for confirming the location of the health care provider, shortening the time for searching for the medial equipment or the patient, recording the number of consultation times of the patient, and the like. In this case, the display device 44 may display the location of the health care provider, the patient, or the medical equipment. Furthermore, the transmission device 20 may be attached to a worker who moves in an office. Accordingly, this configuration can be useful for managing attendance of the worker, confirming the location of the worker, recording the number of times of communication between staff and their boss, and the like. In this case, the display device 44 may display the location of the worker. In addition to the examples mentioned above, the transmission device 20 may be attached to any mobile equipment whose location needs to be confirmed.

The number of transmitters forming the transmission device 20 is not limited to two. Three or more transmitters may be arranged such that non-uniformity of directivities of transmission radio waves can be compensated for. In a similar manner, the number of receivers forming the reception device 120 is not limited to two. Three or more receivers may be arranged such that non-uniformity of directivities of reception radio waves can be compensated for.

The embodiments described above are intended to facilitate understanding of the present disclosure, and are not intended to be interpreted as limiting the present disclosure. The present disclosure may be modified/improved without necessarily departing from the scope of the present disclosure. The present disclosure also encompasses equivalents thereof. That is, design changes added as desired to the embodiments by those skilled in the art also fall within the scope of the present disclosure as long as the characteristics of the present disclosure are provided. Furthermore, the elements of the embodiments may be combined with each other as long as they are technically possible, and combinations of those are also included in the scope of the present disclosure as long as the combinations include the characteristics of the present disclosure.

REFERENCE SIGNS LIST

10 . . . position estimation system, 20 . . . transmission device, 21 and 22 . . . transmitter, 31, 32, 33, 34, 35, 36, 37, and 38 . . . receiver, 40 . . . computer system, 41 . . . processor, 42 . . . memory resource, 43 . . . communication interface, 44 . . . display device, 50 . . . computer program, 51 . . . estimation tool, 61, 62, 63, 64, 65, 66, 67, and 68 . . . plant facility, 71, 72, 73, and 74 . . . area, 81 and 82 . . . directivity of radio waves, 90 . . . human body, 91 and 92 . . . arm, 93 . . . head part, 101, 102, 103, 104, 105, 106, 107, and 108 . . . position

The invention claimed is:

1. A position estimation system comprising:
a transmission device comprising a plurality of transmitters configured to transmit radio waves, the plurality of transmitters being arranged symmetrically with respect to a reference position such that the plurality of transmitters are configured to compensate for a non-uniformity of directivities and of the transmission of the radio waves;

a plurality of receivers configured to receive the radio waves transmitted from the plurality of transmitters; and a processor configured to estimate a position of the transmission device based on reception strengths of the received radio waves.

2. The position estimation system according to claim 1, wherein each receiver is associated with one of a plurality of groups, each of the groups being associated with a corresponding physical region in which a receiver of the group is located, and wherein the processor is configured to estimate the physical region in which the transmission device is located based on a comparison of the reception strengths of the received radio waves between the groups.

3. The position estimation system according to claim 2, wherein the transmission device is configured to be attached to an operator such that the transmission device moves in a facility as the operator moves in the facility, and wherein the position estimation system further comprises a display configured to display a position of the operator based on the estimated position of the transmission device, and to display an operating status of the facility in association with the displayed position.

4. The position estimation system according to claim 2, wherein the transmission device is configured to be attached to an operator such that the transmission device moves in a facility as the operator moves in the facility, and wherein when the reception strengths of the received radio waves are not sufficient to estimate a position of the operator based on the estimated position of the transmission device, the processor is configured to estimate the position of the operator based on an operating status of the facility.

5. The position estimation system according to claim 2, wherein at least two of the plurality of receivers are installed in one of the physical regions, and wherein the transmission device is configured to pass through the one of the physical regions between the at least two receivers.

6. The position estimation system according to claim 1, wherein the transmission device is configured to be attached to an operator such that the transmission device moves in a facility as the operator moves in the facility, and wherein the position estimation system further comprises a display configured to display a position of the operator based on the estimated position of the transmission device, and to display an operating status of the facility in association with the displayed position.

7. The position estimation system according to claim 1, wherein the transmission device is configured to be attached to an operator such that the transmission device moves in a facility as the operator moves in the facility, and wherein when the reception strengths of the received radio waves are not sufficient to estimate a position of the operator based on the estimated position of the transmission device, the processor is configured to estimate the position of the operator based on an operating status of the facility.

* * * * *